(12) United States Patent
Elghazzawi et al.

(10) Patent No.: US 11,224,738 B2
(45) Date of Patent: Jan. 18, 2022

(54) MEDICAL EQUIPMENT ELECTRODES

(71) Applicant: ZOLL Medical Corporation, Chelmsford, MA (US)

(72) Inventors: Ziad F Elghazzawi, Newton, MA (US); Gary A Freeman, Waltham, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 363 days.

(21) Appl. No.: 16/441,673

(22) Filed: Jun. 14, 2019

(65) Prior Publication Data
US 2019/0314625 A1 Oct. 17, 2019

Related U.S. Application Data

(60) Continuation of application No. 15/715,217, filed on Sep. 26, 2017, now Pat. No. 10,363,409, which is a (Continued)

(51) Int. Cl.
*A61N 1/39* (2006.01)
*A61N 1/04* (2006.01)
(Continued)

(52) U.S. Cl.
CPC ............ *A61N 1/046* (2013.01); *A61B 5/0077* (2013.01); *A61B 5/065* (2013.01); *A61N 1/3904* (2017.08);
(Continued)

(58) Field of Classification Search
CPC .... A61N 1/046; A61N 1/3904; A61N 1/3993; A61N 1/3925; A61N 1/3968;
(Continued)

(56) References Cited

U.S. PATENT DOCUMENTS

| 4,245,233 A | 1/1981 | Lohstroh |
| 4,248,243 A | 2/1981 | Niess et al. |

(Continued)

FOREIGN PATENT DOCUMENTS

| JP | H04227229 | 4/1990 |
| WO | 2001058522 | 8/2001 |

OTHER PUBLICATIONS

International Search Report and Written Opinion, PCT/US2012/050926, dated Jan. 23, 2013, 22 pages.
(Continued)

*Primary Examiner* — Eugene T Wu
(74) *Attorney, Agent, or Firm* — ZOLL Medical Corporation

(57) ABSTRACT

Methods and system for guiding a rescuer in placement of a defibrillation electrode may include initializing one or more cameras disposed on the defibrillation electrode, and capturing image information via the one or more cameras. Each image in a series of images may be acquired by the cameras after a set time interval. The method may include determining a separation distance between the defibrillation electrode and the chest of the patient and comparing the separation distance to a threshold distance. The method may further include determining whether the separation distance is below the threshold distance and, once the separation distance is below the threshold distance, determining a current location of the defibrillation electrode based on the series of images, and providing positioning feedback via at least one output device, wherein the positioning feedback includes instructions to move the defibrillation electrode toward a preferred location on the patient.

22 Claims, 11 Drawing Sheets

Related U.S. Application Data continuation of application No. 14/876,927, filed on Oct. 7, 2015, now Pat. No. 9,802,034, which is a division of application No. 13/558,905, filed on Jul. 26, 2012, now Pat. No. 9,180,288.

(60) Provisional application No. 61/530,043, filed on Sep. 1, 2011.

(51) Int. Cl.
*A61B 5/06* (2006.01)
*A61B 5/00* (2006.01)

(52) U.S. Cl.
CPC .......... *A61N 1/3925* (2013.01); *A61N 1/3968* (2013.01); *A61N 1/3993* (2013.01); *A61B 5/684* (2013.01); *A61N 1/39044* (2017.08)

(58) Field of Classification Search
CPC .. A61N 1/39044; A61B 5/065; A61B 5/0077; A61B 5/684
See application file for complete search history.

(56) References Cited

U.S. PATENT DOCUMENTS

| | | | |
|---|---|---|---|
| 4,255,238 A | 3/1981 | Delapierre et al. |
| 4,266,263 A | 5/1981 | Haberl et al. |
| 4,290,474 A | 9/1981 | Medovar et al. |
| 4,291,321 A | 9/1981 | Pfleiderer et al. |
| 4,300,091 A | 11/1981 | Schade, Jr. |
| 4,303,073 A | 12/1981 | Archibald |
| 4,326,927 A | 4/1982 | Stetter et al. |
| 4,341,944 A | 7/1982 | Breen |
| 4,347,478 A | 8/1982 | Heerens et al. |
| 4,348,685 A | 9/1982 | Jaouannet et al. |
| 4,382,826 A | 5/1983 | Pfleiderer et al. |
| 4,394,239 A | 7/1983 | Kitzelmann et al. |
| 4,394,765 A | 7/1983 | Reimpell et al. |
| 4,427,052 A | 1/1984 | Garfinkle |
| 4,440,726 A | 4/1984 | Coulson |
| 4,442,340 A | 4/1984 | Kawabata et al. |
| 4,488,029 A | 12/1984 | Liechti et al. |
| 4,491,951 A | 1/1985 | Dunn |
| 4,494,541 A | 1/1985 | Archibald |
| 4,500,402 A | 2/1985 | Miles et al. |
| 4,536,636 A | 8/1985 | Opprecht et al. |
| 4,566,950 A | 1/1986 | Miles |
| 4,591,687 A | 5/1986 | Urech |
| 4,772,851 A | 9/1988 | Schattschneider |
| 4,780,663 A | 10/1988 | Mulder |
| 5,042,498 A | 8/1991 | Dukes |
| 5,184,620 A | 2/1993 | Cudahy et al. |
| 5,187,371 A | 2/1993 | Matsui et al. |
| 5,231,422 A | 7/1993 | Takeuchi et al. |
| 5,298,146 A | 3/1994 | Braden et al. |
| 5,395,493 A | 3/1995 | Pinkowski |
| 5,538,620 A | 7/1996 | Nikolskaja |
| 5,574,311 A | 11/1996 | Matsuda |
| 5,583,527 A | 12/1996 | Fujisaki et al. |
| 5,616,061 A | 4/1997 | Potter |
| 5,625,382 A | 4/1997 | Ebihara et al. |
| 5,628,663 A | 5/1997 | Potter |
| 5,637,952 A | 6/1997 | Tischer |
| 5,654,114 A | 8/1997 | Kubota et al. |
| 5,666,019 A | 9/1997 | Potter |
| 5,745,085 A | 4/1998 | Tomio et al. |
| 5,786,794 A | 7/1998 | Kishi et al. |
| 5,825,345 A | 10/1998 | Takahama et al. |
| 5,843,798 A | 12/1998 | Matsuda |
| 5,879,308 A | 3/1999 | Raesaenen |
| 5,973,655 A | 10/1999 | Fujisaki et al. |
| 6,023,258 A | 2/2000 | Kuriyama et al. |
| 6,107,728 A | 8/2000 | Spindt et al. |
| 6,116,257 A | 9/2000 | Shinichi et al. |
| 6,259,945 B1 | 7/2001 | Epstein et al. |
| 7,020,508 B2 | 3/2006 | Stivoric et al. |
| 7,149,576 B1 | 12/2006 | Baura et al. |
| 7,277,752 B2 | 10/2007 | Matos |
| 7,421,300 B2 | 9/2008 | Smits |
| 7,706,878 B2* | 4/2010 | Freeman .............. A61B 5/4848 607/6 |
| 7,715,913 B1 | 5/2010 | Froman et al. |
| 7,769,465 B2 | 8/2010 | Matos |
| 8,208,997 B2 | 6/2012 | Nilsson et al. |
| 8,355,774 B2 | 1/2013 | Markowitz et al. |
| 8,903,477 B2 | 12/2014 | Berkner |
| 8,948,885 B2 | 2/2015 | Russell |
| 9,067,080 B2 | 6/2015 | Einy |
| 9,737,723 B2 | 8/2017 | Einy |
| 2004/0015191 A1 | 1/2004 | Otman et al. |
| 2004/0267325 A1 | 12/2004 | Geheb et al. |
| 2006/0161147 A1 | 7/2006 | Privitera et al. |
| 2007/0156126 A1 | 7/2007 | Flaherty |
| 2009/0240297 A1* | 9/2009 | Shavit .................... G16H 40/63 607/5 |
| 2010/0069735 A1* | 3/2010 | Berkner ................. A61B 5/684 600/382 |
| 2010/0081950 A1 | 4/2010 | Reinstadtler |
| 2010/0241181 A1 | 9/2010 | Savage et al. |
| 2011/0040217 A1 | 2/2011 | Centen |
| 2012/0229661 A1 | 9/2012 | Sekiguchi et al. |

OTHER PUBLICATIONS

Supplementary European Search Report, EP12827824, dated Feb. 24, 2015, 9 pages.

\* cited by examiner

MEDICAL EQUIPMENT ELECTRODES

CLAIM OF PRIORITY

This application is a continuation under 35 U.S.C. § 120 of U.S. patent application Ser. No. 15/715,217, filed on Sep. 26, 2017, which is a continuation of U.S. patent application Ser. No. 14/876,927, filed on Oct. 7, 2015, which issued as U.S. Pat. No. 9,802,034 on Oct. 31, 2017, which is a divisional under 35 U.S.C. § 120 of U.S. patent application Ser. No. 13/558,905, filed on Jul. 26, 2012, and issued as U.S. Pat. No. 9,180,288 on Nov. 10, 2015, which claims the benefit under 35 U.S.C. § 119(e) to U.S. Provisional Patent Application No. 61/530,043, filed on Sep. 1, 2011. All subject matter set forth in the above-referenced applications is hereby incorporated by reference in its entirety into the present application as if fully set forth herein.

TECHNICAL FIELD

Cardiac therapy electrodes and techniques for testing application of the electrodes to a victim are described herein.

BACKGROUND

External defibrillators frequently include a pair of "hands-free" disposable electrodes, which are essentially flexible pads that are adhered to the skin of a subject having a cardiac event (i.e., used transcutaneously). The hands-free electrodes can be of the type that are adhered to a subject, rather than paddles that are held by a rescuer during defibrillation. Hands-free disposable electrodes typically include a non-conductive backing layer, a conductive layer, formed from a thin sheet of metal (e.g. tin or silver) or a conductive ink (e.g. silver-chloride) printed on a substrate, and a liquid or solid electrically conductive gel covering the electrically conductive layer so that electrical current passes through the gel to the subject's body. The area of contact between the gel and the subject's body where current is delivered is referred to herein as the "treatment area".

SUMMARY

In some aspects, an electrode includes a camera configured to generate image information related to the position of the electrode relative to an subject's chest.

In some aspects, a method can include receiving image information from a camera in an electrode; determining information about a position of the electrode based on the image information; and providing an indication relating to positioning of the electrode.

In some aspects, a device can include an electronic interface arranged to receive image information from a camera in an electrode, the image information providing information from which information about the position of the electrode relative to an subject's chest can be obtained and provide feedback to a rescuer about the positioning of the electrode based on the received image information.

In some aspects, a device includes a first therapy electrode for use with a defibrillation device. The first therapy electrode includes a first conductive element of the first therapy electrode configured to accept an electrical defibrillation pulse from the defibrillation device and spread the electrical pulse across the conductive element, from which it is delivered to the patient's chest and a second conductive element of the first therapy electrode that is separate from the first conductive element and configured to provide an electrical contact to the patient's chest. The first therapy electrode also includes a first electrical lead of the first therapy electrode connected to the first conductive element of the first therapy electrode and a second electrical lead of the first therapy electrode connected to the second conductive element of the first therapy electrode, the first and second electrical leads of the first therapy electrode providing an output from which information indicative of whether the first therapy electrode is affixed to the patient's chest can be obtained.

In some additional aspects, a method includes determining an impedance between a first conductive element and a second conductive element of a first therapy electrode and comparing, by a computing device, the impedance to a threshold to determine whether the first therapy electrode is affixed to a patient's chest.

Other features and advantages of the invention will be apparent from the drawings, detailed description, and claims.

DETAILED DESCRIPTION

Figure 1:
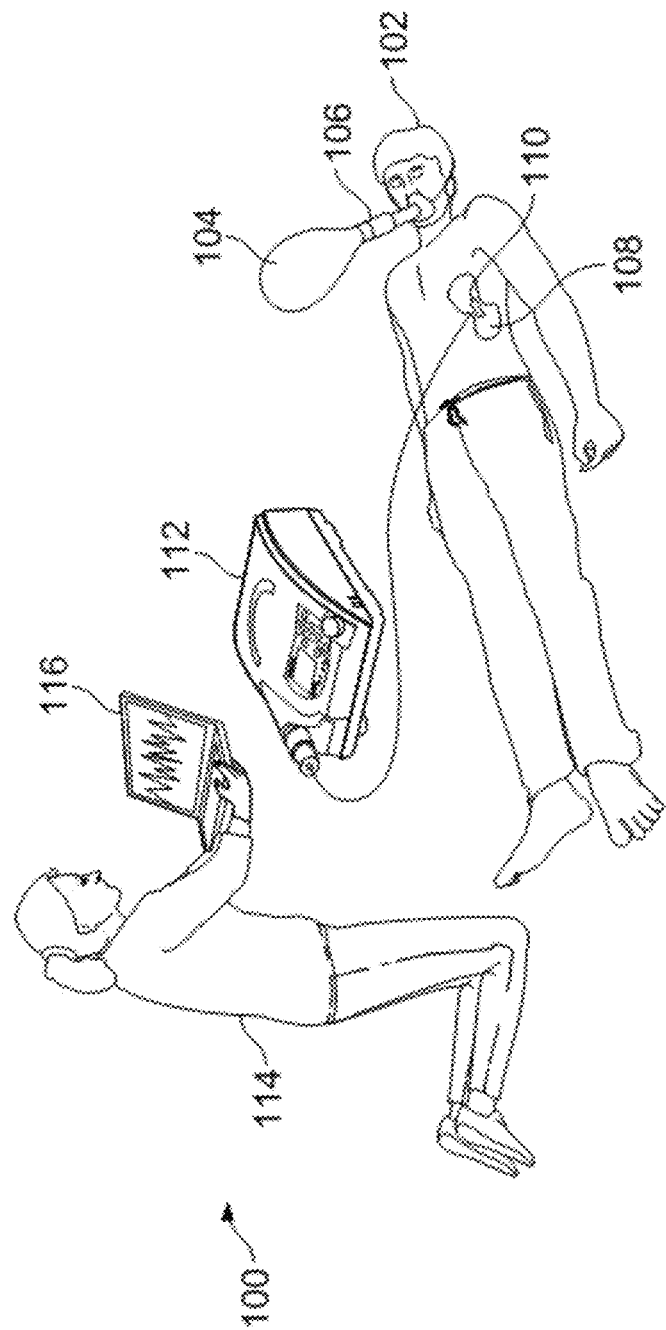
FIG. 1 is a schematic diagram of a system for responding to an emergency medical condition.

FIG. 1 shows a system 100 for responding to an emergency medical condition of a victim 102. In general, system 100 includes various portable devices for monitoring on-site care given to a victim 102 of an emergency situation. The rescuer 114 in this example is interacting with a computing device in the form of a touchscreen tablet 116 that includes a graphical display by which to report information to the rescuer 114, and may have an input mechanism such as a keyboard or a touchscreen by which the rescuer 114 may enter data into the system 100. The tablet 116 may also include a wireless transceiver for communicating with a wireless network, such as a 3G or 4G chipset that permits long distance communication over cellular data networks, and further through the internet.

Separately, a portable defibrillator 112 is shown in a deployed state and is connected to the victim 102. In addition to providing defibrillation, the defibrillator 112 may serve as a subject monitor via a variety of sensors or sensor packages. For example, as shown here, electrodes 108 connected to the defibrillator 112 have been applied to the victim 102 so that electrical shocking pulses may be provided to the electrodes in an effort to defibrillate the victim 102, and electrocardiogram (ECG) signals may be read from the victim 102. Further examples of use of the portable defibrillator are described, for example, in Ser. No. 13/398, 280 filed on Feb. 16, 2012 and entitled "Coordinated Resuscitation Perfusion Support", the contents of which are hereby incorporated by reference. The defibrillator operates according to a set of configurations stored on the defibrillator. The defibrillator 112 may include an accelerometer assembly 110 configured to identify a vertical displacement caused by CPR compressions and provide feedback to the rescuer based on the measured displacements. The defibrillator can additionally be provided with a ventilation bag 104 that includes an airflow sensor 106 to identify a rate at which ventilation is occurring with the victim. The defibrillator 112 may communicate through a short range wireless data connection with the tablet 116 to provide to the tablet 116 status information, such as information received through the electrode assembly 108, including ECG information for the victim 102. Also, the defibrillator 112 can send information about the performance of chest compressions, such as depth and rate information for the chest compressions.

Defibrillators such as defibrillator 112 shown in FIG. 1 often utilize two electrodes 108, commonly referred to as sternum and apex electrodes. The electrodes 108 can be hands-free electrodes configured to deliver a shock to a victim. In order to deliver the shock, an electrical current path is formed between the electrode and the victim. Systems and methods described herein provide information indicative of whether the electrodes 108 are adequately affixed to the victim 102 to provide such an electrical current path between the electrode 108 and the victim 102. Providing a rescuer 114 with information about whether the electrodes 108 are adequately affixed to form the current path between the defibrillator 112 and the victim 102, can provide the advantage of preemptively allowing the rescuer 114 to re-attach the electrodes 108 prior to delivery of the defibrillation shock.

Figure 2A:
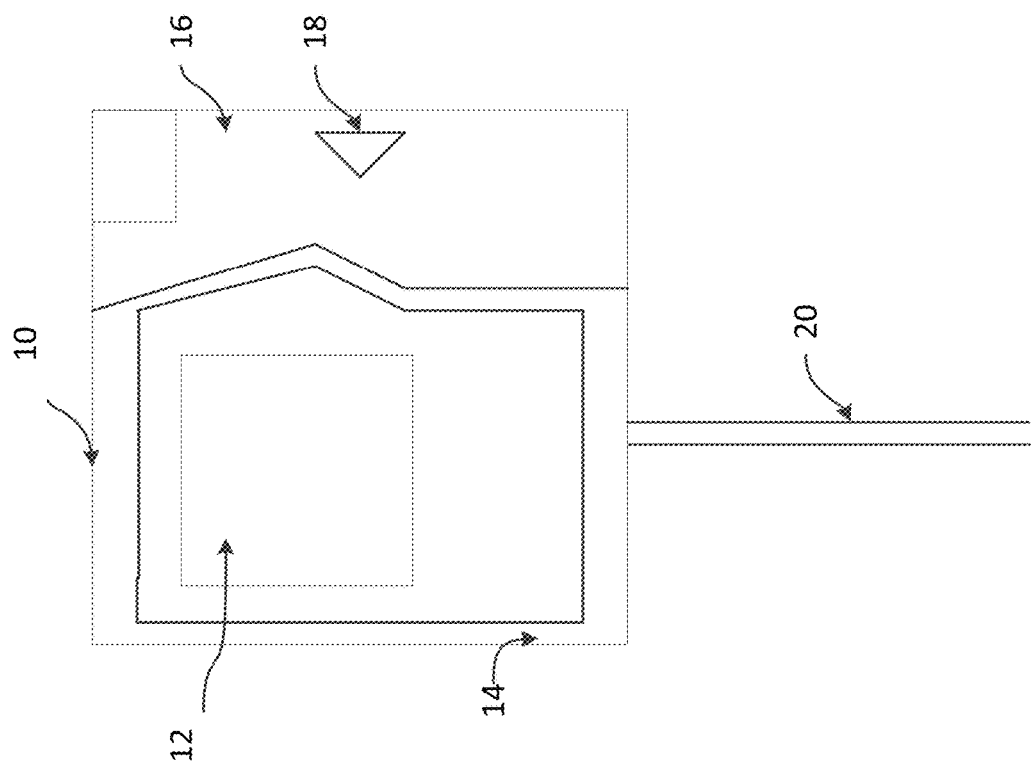
FIG. 2A is a schematic diagram of the exterior of an assembled electrode package.

FIG. 2A shows an assembled electrode package 10 with multi-conductor electrical lead 20 and label 12 according to an example embodiment of the invention. The package is opened by grasping the loose flaps 16 at arrow label 18, and peeling back the top flap. As the flaps are pulled apart, the releasable peripheral adhesive 14 separates.

Figure 2B:
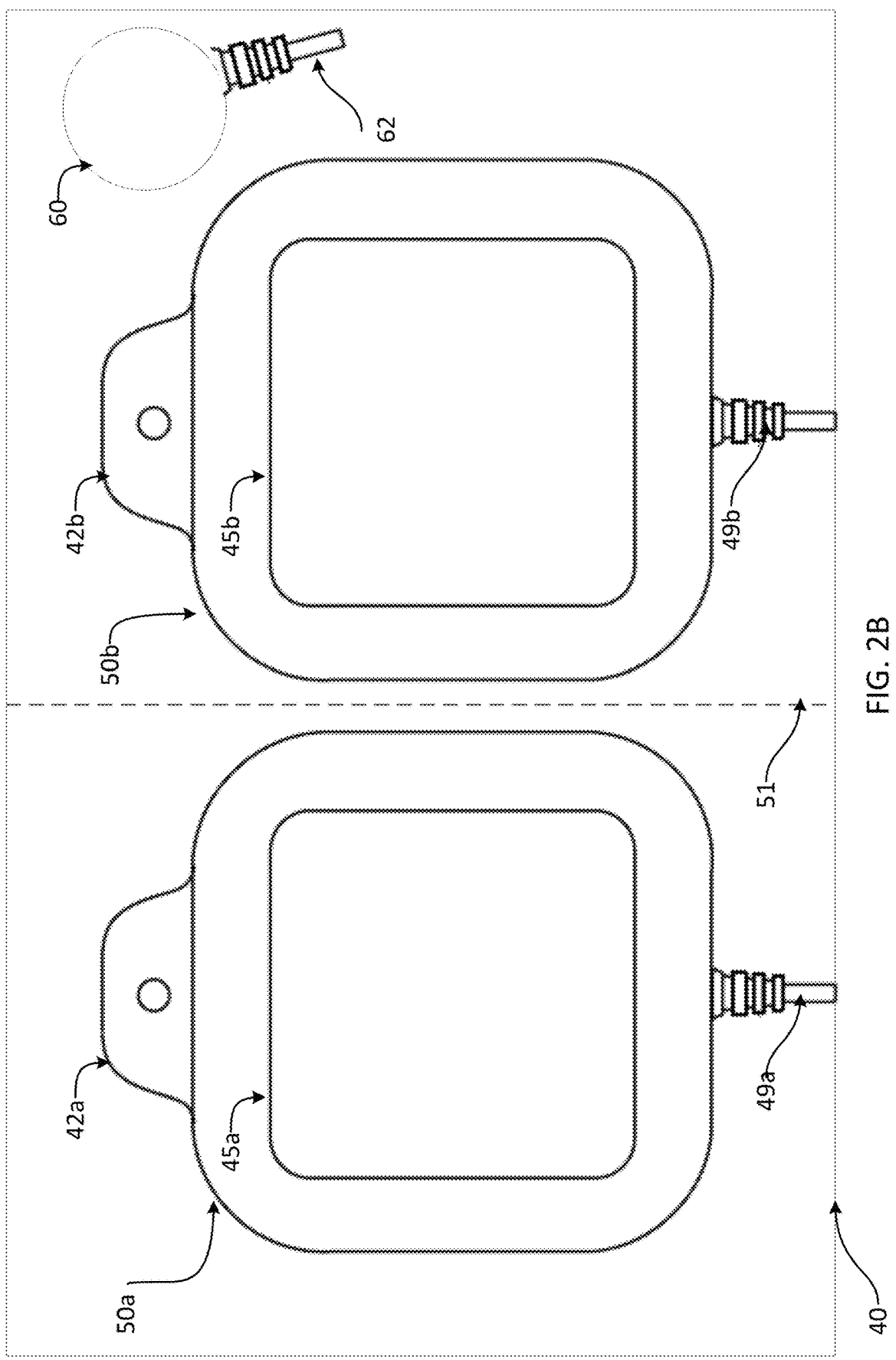
FIG. 2B is a schematic diagram of the contents of the package after opening.

FIG. 2B shows a view of the electrodes 50a and 50b, an accelerometer 60, and styrene sheet 40 after removal from the electrode package 10 according to an example embodiment of the invention. Before the package is opened, the styrene sheet 40 is folded along fold line 51 in the form of a closed book, with the electrodes 50a and 50b and accelerometer 60 peelably attached to the interior facing surfaces of the book. On opening the package, the book is unfolded, so that the electrodes and accelerometer are presented to the user as shown in FIG. 2B.

In an embodiment, electrodes 50a and 50b are designed to be peeled from the styrene sheet 40 using tabs 42a and 42b, and applied to the subject's chest. The accelerometer 60 is also peeled from the sheet 40, and applied to the front of the subject's chest at the sternum location at which CPR compressions are delivered. The accelerometer works with electronics in a defibrillator to determine the depth of compressions during CPR. ECG electrodes (not shown) are built into one of electrode 50a or 50b (each is located at approximately the corners of the triangular shape of the electrode). Labels 45a and 45b instruct the user in how to attach the electrodes and accelerometer. Each electrode has a wire lead 49a and 49b that extends to a connector (not shown) for connection to the defibrillator. Lead 62 from the accelerometer and leads from the ECG electrodes (not shown) also extend to the same connector (not shown). All of the leads are joined together in one multi-conductor lead 20 (FIG. 1).

Figure 3:
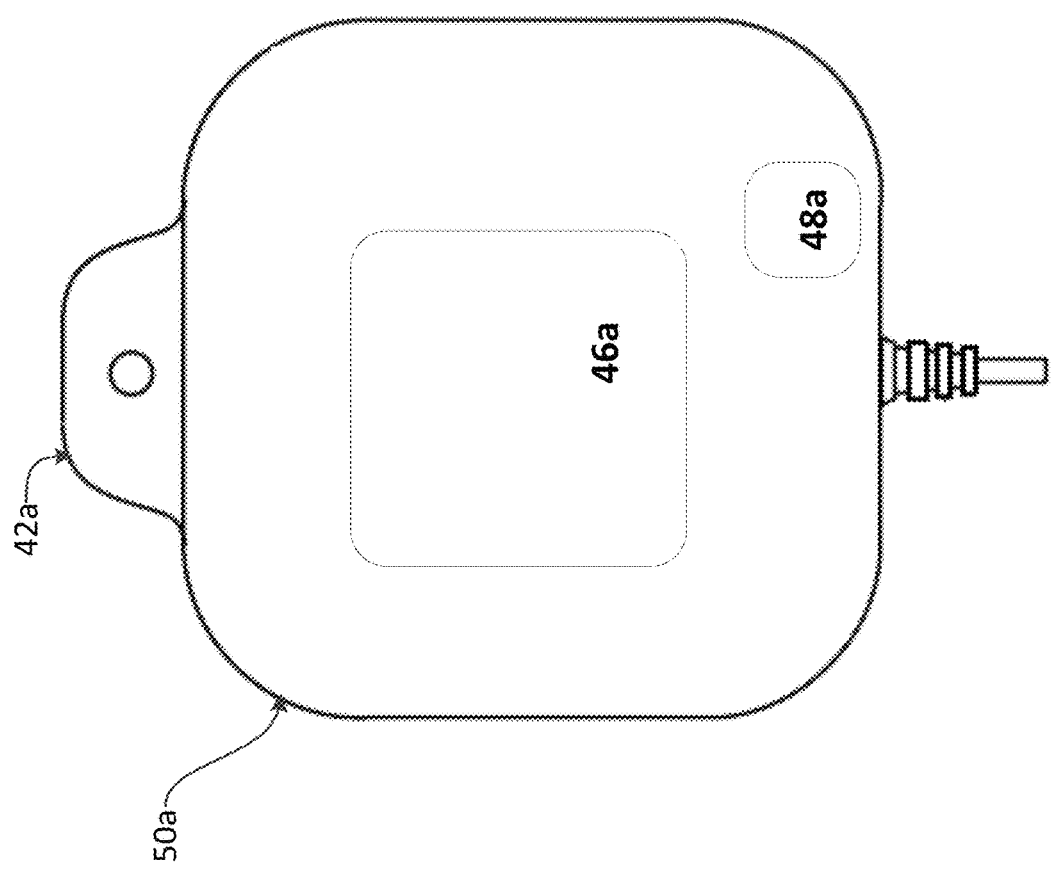
FIG. 3 is a schematic diagram of one of the electrodes.

FIG. 3 shows the top surface of electrode 50a after removal from sheet 40 (e.g., the side of electrode 50a that is configured to be attached to the surface of a subject's skin) according to an example embodiment of the invention. Electrode 50a includes two electrically conductive (e.g., metallic) components, 46a and 48a. Component 46a is configured to receive a defibrillation pulse from the defibrillator and spread the electrical pulse across the electrically conductive element, from which it is delivered to the subject's chest. Component 48a is a testing contact that is configured to provide information indicative of whether the first therapy electrode is affixed to the subject's chest can be obtained by measurement of an impedance between the two components 46a and 48a.

Electrode 50a includes an electrically non-conductive portion that encapsulates a portion of a conductive electrically conductive component 46a. Those portions of the electrically conductive component 46a not encapsulated in the non-conductive portion are on the top surface (the subject side) of the electrode 50a and deliver electrical current to a subject via an electrolyte (not shown) that is between the electrically conductive component 46a and a subject. Accordingly, these portions may be referred to herein as "current delivery surfaces".

The electrically conductive component 46a can be configured such that the treatment area is at least 2.33 sq. inches (15 sq. cm), with a combined treatment area associated with two electrodes (the sternum electrode and the apex electrode) of 6.98 sq. inches (45 sq. cm) for pediatric electrodes; and 7.75 square inches (50 square cm), with a combined treatment area associated with two electrodes (the sternum electrode and the apex electrode) of at least 23.25 square inches (150 square cm). For example, the electrically conductive components can be configured in accordance with AAMI DF-80 and international specifications. For example, in an embodiment, the treatment area associated with each pediatric electrode is 7.56 sq. inches (22.5 sq. cm) and for all other electrodes 11.63 square inches (75 square cm.) per electrode. The area outside of the treatment area (which is comprised of the non-conductive material) should be of sufficient dimensions as to prevent lateral discharge of current to the outer edge of the electrode and to enable attachment of an adhesive ring to which a coupling layer such as hydrogel is attached. Exemplary dimensions (length and width) for the electrically conductive component, treatment area and composite structure are described, for example in U.S. patent application Ser. No. 12/825,143, filed on Jun. 28, 2010 and entitled "Defibrillation Electrodes," the contents of which are hereby incorporated by reference.

As described above, electrode 50a also includes a testing contact 48a. The testing contacts 48a and 48b can be similar in size to a regular ECG monitoring electrode. The testing contact 48a is on the top surface (the subject side) of the electrode 50a and is not encapsulated in the non-conductive portion. Thus, after attachment of the electrode 50a to the subject, the electrode 50a is in contact with the subject via an electrolyte (not shown) that is between the testing contact 48a and the subject. The testing contact is formed of metal or another conductive material and can be used to measure a voltage or current. An electrical lead extends from the testing contact 48a.

Construction of the electrode 50b is similar to that of the electrode 50a, hence separate views are not provided.

Figure 4:
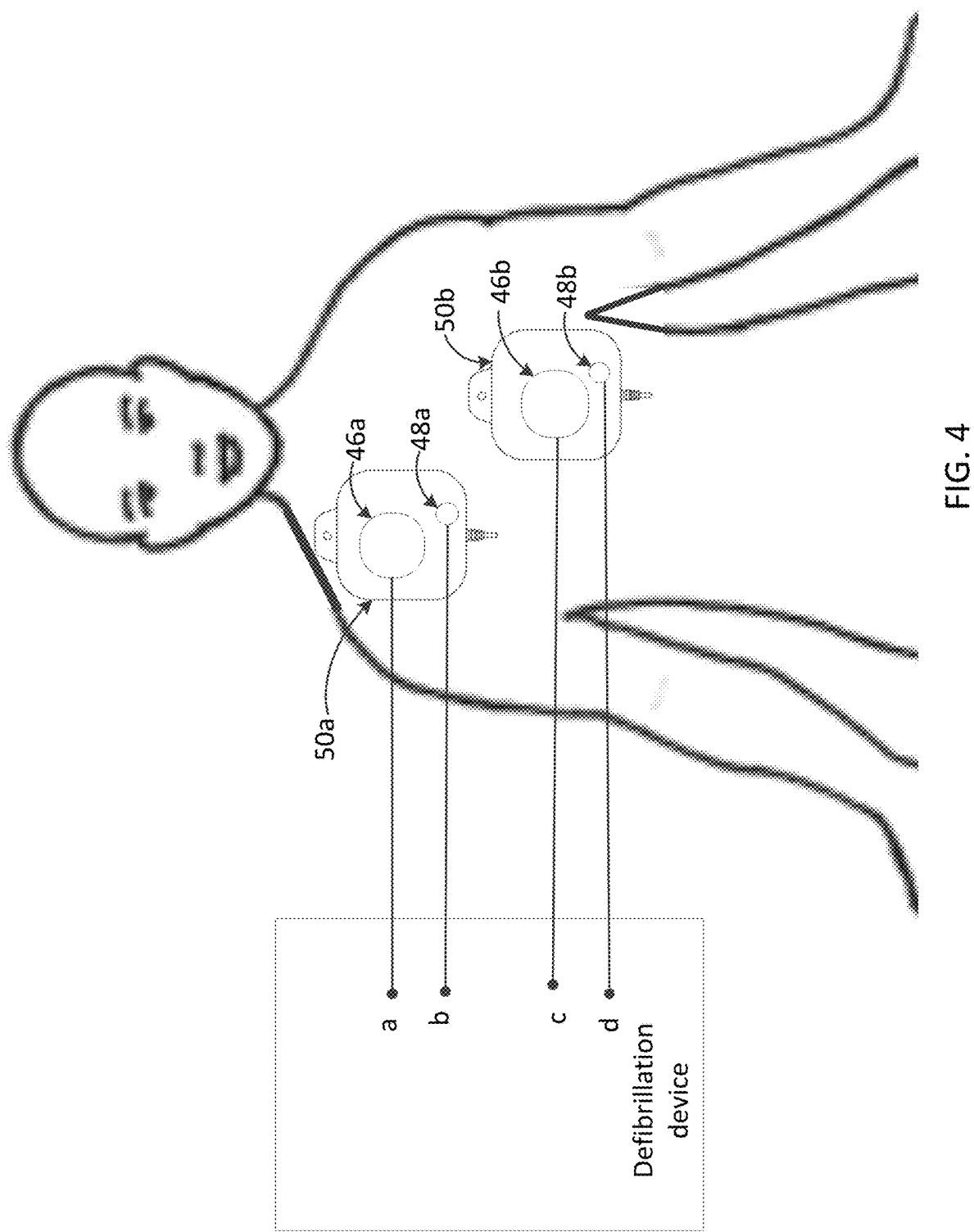
FIG. 4 is a schematic diagram of the electrodes after attachment to a subject.

In operation, as shown in FIG. 4, an impedance measured between the electrically conductive component 46a and the testing contact 48a can be used to determine whether the electrode 50a is sufficiently attached to the subject (e.g., by measuring an impedance between nodes 'a' and 'b' as shown in FIG. 4). More particularly, when the electrode 50a is not sufficiently attached to the subject (e.g., not in contact with the subject's skin), the impedance between the electrically conductive component 46a and the testing contact 48a will be significantly higher than when the electrode 50a is sufficiently attached to the subject. For example, an impedance of greater than 10 kOhms can indicate that the electrode is not sufficiently attached to the subject. More particularly, when the electrode is not appropriately attached, a current path does not exist through the subject's body. Rather, air and/or a non-conductive material may separate the two electrodes resulting in a high impedance (e.g., an impedance of greater than 10 kOhms).

In some examples, if an impedance of less than 10 kOhms is measured between the electrically conductive component 46a and the testing contact 48a, the system can determine that the electrode is attached to the subject. For example, an impedance measurement of 1 kOhm to 10 kOhms between the electrically conductive component 46a and the testing contact 48a can indicate proper attachment of the electrode to the subject. Thus, by measuring the impedance between the electrically conductive component 46a and the testing contact 48a the system can determine whether the electrode 50a is attached correctly and can provide feedback to the user regarding the attachment of the electrode (e.g., whether the user has correctly attached the electrode and can continue with treatment of the subject or whether the rescuer needs to take further actions to correctly secure the electrode to the subject).

Similarly, an impedance can be measured between the electrically conductive component 46b and the testing contact 48b of electrode 50b (e.g., between nodes 'c' and 'd') to determine whether the electrode 50b is sufficiently attached to the subject and appropriate feedback can be provided to the rescuer.

In some examples, in addition to testing the attachment of each of the electrodes 50a and 50b to the subject, the current flow between the two electrodes can also be tested. For example, after attachment of both electrodes, an impedance can be measured between the electrically conductive components 46a and 46b of electrodes 50a and 50b (e.g., between nodes 'a' and 'c'). Based on the measured impedance value, the system can determine whether the proper contact exists between the electrodes and the subject. For example, if only a small portion of the electrically conductive component 46a or 46b is in contact with the subject's skin (e.g., the electrode needs to be further pressed down onto the subject's skin), then the resistance between the two electrically conductive components 46a and 46b will be greater. For example, a measurement of less than 300 Ohms impedance between the electrically conductive components 46a and 46b can indicate proper attachment of the electrode to the subject. If a higher impedance is measured (and the system has determined both electrodes have been applied to the subject based on the measurements between the electrically conductive components and the testing electrodes, then the system can instruct the rescuer to smooth the electrode or press more firmly on the electrode to form a better contact with the subject's skin.

Figure 5:
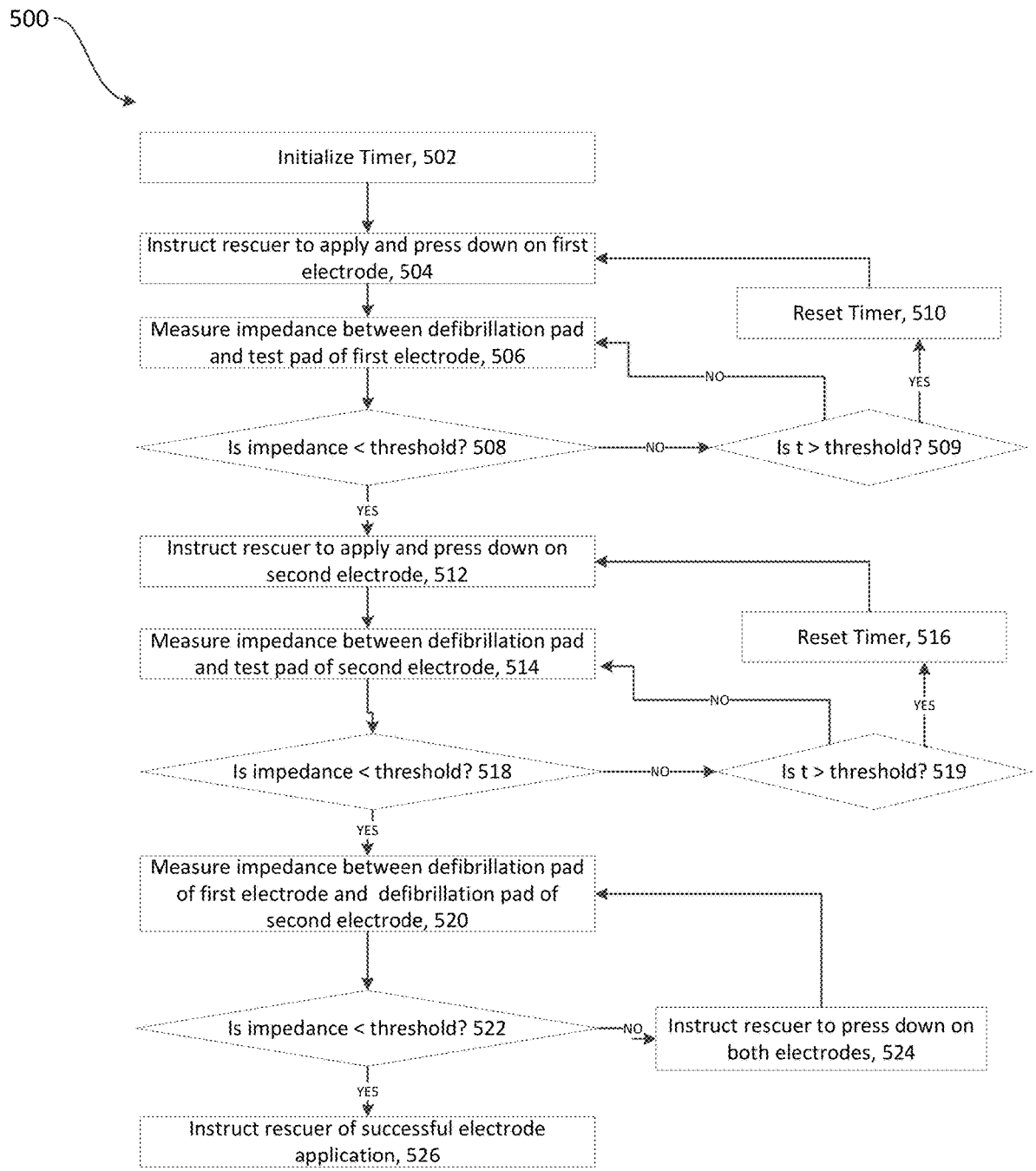
FIG. 5 is a flow chart of a process for testing the attachment of the electrodes to the subject.

FIG. 5 is a flow chart of a process 100 for testing the attachment of electrodes to a subject and providing feedback to a rescuer regarding attachment of the electrodes according to an example embodiment of the invention. After the electrodes are attached to a defibrillation device, the defibrillation device initializes a timer (502) and instructs the rescuer to apply and press down on a first electrode (504). For example, the defibrillation device can provide audio and/or visual instructions to the rescuer regarding proper removal of the electrode from the backing and attachment to the victim. In some particular examples, the defibrillation device can include a user interface capable of displaying a video showing an animation or short video clip of how the electrode should be removed from the backing and where the electrode should be applied on the subject.

The process measures an impedance between the electrically conductive component of the electrode used to deliver a defibrillation current and the test electrode (506). Based on the measurement, the defibrillation device determines whether the impedance is less than a preset threshold, for example less than 10 k-Ohms (508).

If the impedance is not less than the preset impedance threshold (e.g., the preset impedance is greater than the impedance threshold), the system determines that the electrode is not correctly affixed to the subject and determines whether the elapsed time, t, is greater than a threshold (509). Exemplary timing thresholds can be between 5 to 10 seconds to allow the rescuer sufficient time to attach the electrode prior to interrupting the rescuer with further instructions. If the time is not greater than a threshold, the system returns to measuring the impedance (506) to allow the rescuer additional time to attach the electrode. If the time is greater than the threshold, the system resets the timer (510) and provides instructions to the rescuer regarding the application of the electrode.

If, as a result of determination 508, the impedance is less than the impedance threshold, the system instructs the rescuer to apply and press down on a second electrode (512). For example, the defibrillation device can provide audio and/or visual instructions to the user regarding proper removal of the electrode from the backing and attachment to the victim as described above. The defibrillation device measures an impedance between the electrically conductive component of the second electrode used to deliver a defibrillation current and the test electrode (514). Based on the measurement, the defibrillation device determines whether the impedance is less than a preset threshold, for example less than 10 kOhms (518). If the impedance is not less than the impedance threshold (e.g., the impedance is greater than the impedance threshold), the system determines that the second electrode is not correctly affixed to the subject and determines whether the elapsed time, t, is greater than the timing threshold (519). If the time is not greater than a threshold, the system returns to measuring the impedance (514) to allow the rescuer additional time to attach the electrode. If the time is greater than the threshold, the system resets the timer (516) and provides instructions to the rescuer regarding the application of the electrode (512).

If, as a result of determination 518, the impedance is less than the impedance threshold, the system measures an impedance between the two defibrillation electrodes of the first and second electrodes (520) and determines whether the impedance is smaller than a second threshold (e.g., an electrode to electrode threshold). For example, the threshold can be from about 250 to about 300 Ohms. If the measured impedance is greater than the threshold, the system instructs the rescuer to press down on both of the electrodes to ensure good contact is formed with the victim's skin (524) and returns to measuring the impedance (520). If the measured impedance is less than the threshold, the system provides feedback to the rescuer informing the rescuer that the electrodes have been applied successfully (526).

Figure 6:
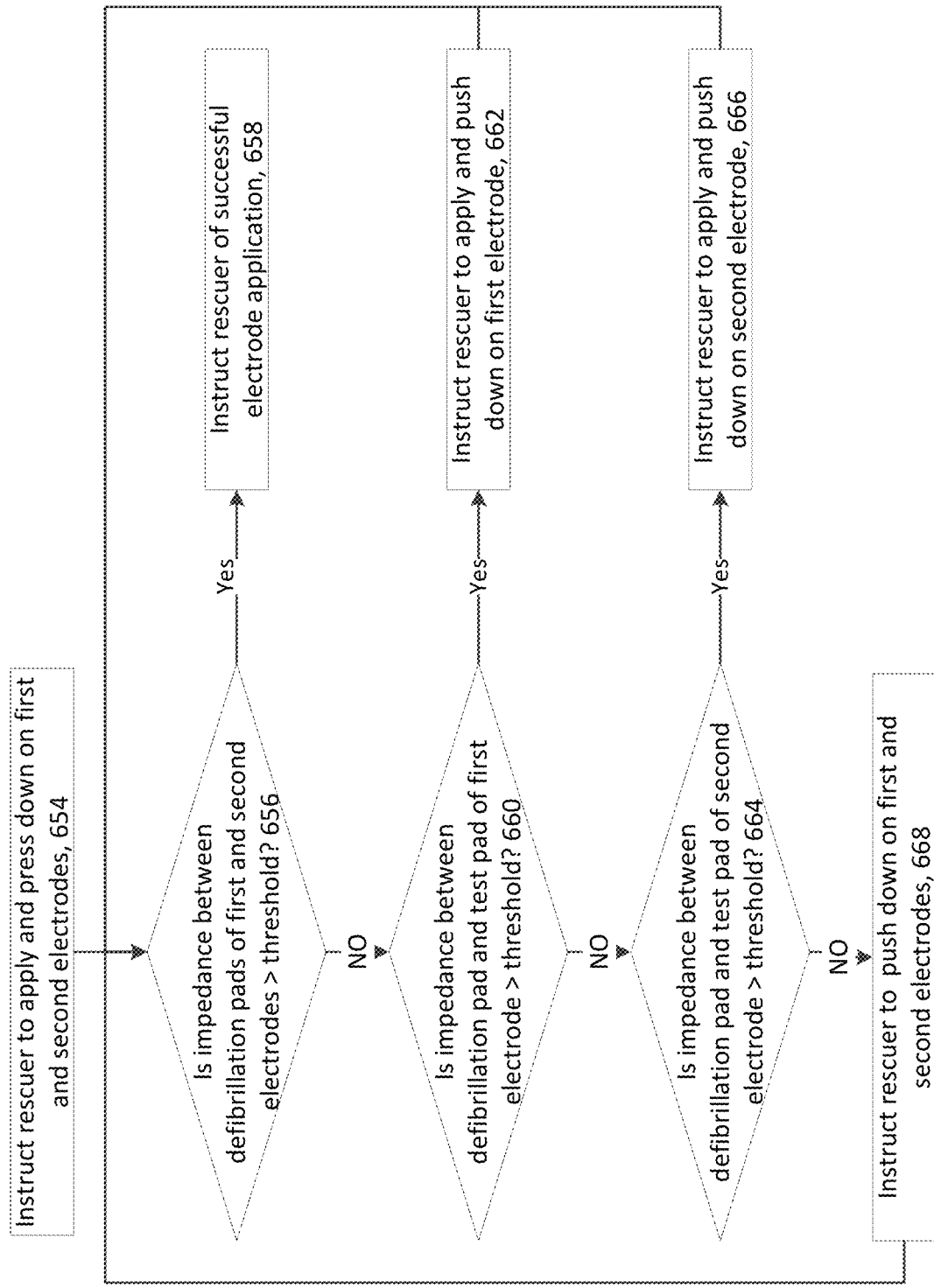
FIG. 6 is a flow chart of a process for testing the attachment of the electrodes to the subject.

FIG. 6 is a flow chart of a process 650 for testing the attachment of defibrillation electrodes to a subject and providing feedback to a rescuer regarding the attachment of the electrodes according to an example embodiment of the invention. In contrast to the example described in relation to FIG. 5, the process of FIG. 6 provides less detailed instruction to the rescuer and could be beneficial for experienced rescuers such as emergency personnel. After the electrodes are attached to a defibrillation device, the defibrillation device instructs the rescuer to apply and press down on both the first and second electrodes (654). Based on a measurement of the impedance between the defibrillation pads of the first and second electrodes, the defibrillation device determines whether the impedance is less than a preset threshold, for example less than 300 Ohms (656). If the impedance is less than the threshold, the system instructs the user of successful electrode application (658). If the impedance is not less than the threshold, the system determines, based on a measurement of an impedance between the defibrillation pad of the first electrode and the test electrode of the first electrode, whether the impedance is less than a second, different threshold (660). If the impedance is greater than the threshold, the system instructs the rescuer to apply and push down on the first electrode (662) and returns to determination 656. If the impedance is less than the threshold, the system determines, based on a measurement of impedance between the defibrillation pad of the second electrode and the test electrode of the second electrode, whether the impedance is less than the second threshold (664). If the impedance is greater than the threshold, the system instructs the rescuer to apply and push down on the second electrode (666) and returns to determination 656. If the impedance is less than the threshold, the system determines that both electrodes have been applied to the subject but adequate contact has not been made with the subject's skin and the system instructs the rescuer to push or smooth both electrodes (668) and returns to determination 656.

Figure 7:
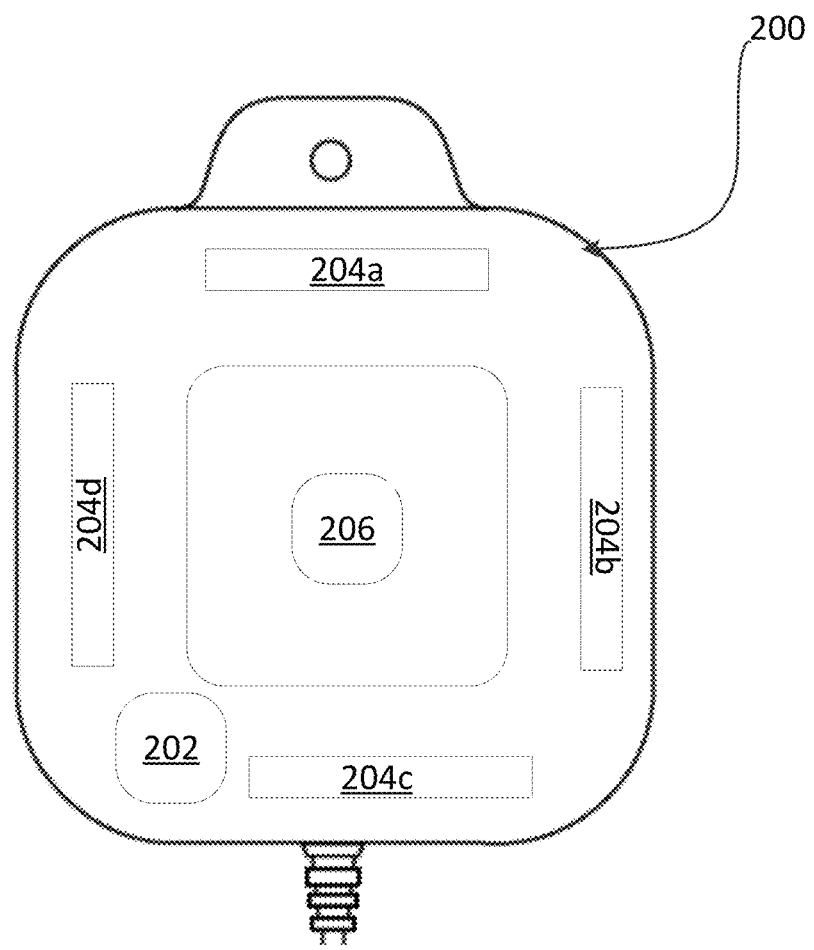
FIG. 7 is a schematic diagram of an electrode.

FIG. 7 shows an electrode 200 configured to assist the rescuer in positioning the electrode 200 on a victim according to an example embodiment of the invention. Rescuers such as lay rescuers may be uncertain about the placement of defibrillation electrodes on a victim. Incorrect placement of the electrodes can reduce the effectiveness of the electrical shock delivered to the victim. In some examples, a rescuer's concern about whether the electrode is correctly positioned can result in the rescuer taking additional time to verify the placement of the electrode (e.g., relative to a placement shown in an instruction manual) which may result in a delay of administration of CPR and/or delivery of a defibrillation shock. Any delay in CPR administration and/or delivery of a defibrillation shock can reduce the effectiveness of the treatment. As such, electrode 200 includes components to provide guidance about the placement of the electrode to the rescuer while the rescuer is in the process of positioning and affixing the electrode 200 to the victim.

More particularly, electrode 200 includes a camera 202 such as a still image digital camera or a video camera. Camera 202 captures image information (e.g., still images taken at predetermined time intervals or video data) and provide the image information to a processor or computing device via an electronic interface. The processor or computing device can be included in a defibrillation device and can be communicatively coupled to the camera by a wired connection or wirelessly such that the processor or computing device can receive image information from the camera 202. Based on the received image information the processor or computing device determines a location of the electrode 200 relative to the victim's body and determines if the rescuer should reposition the electrode prior to application of the electrode 200 (e.g., by determining an x offset value and a y offset value relative to a desired location). The processor or computing device provides information about the position of the electrode or desired direction in which the electrode should be moved to multiple positioning indicators 204*a*, 204*b*, 204*c*, 204*d*, and 206 on the electrode 200 that are configured to provide feedback to the rescuer about whether the electrode is in the correct location relative to the victim. For example, positioning indicators 204*a*, 204*b*, 204*c*, 204*d*, and 206 can include one or more light emitting diodes. Indicators 204*a*, 204*b*, 204*c*, 204*d* can be illuminated to indicate a direction in which the rescuer should move the electrode and indicator 206 can be illuminated to indicate when the electrode 200 is correctly positioned and should be affixed to the victim. For example, electrode 200 includes indicator 204*a* (e.g., an LED) positioned on a top portion of the top surface of the therapy electrode to provide information indicating the electrode should be moved toward the subject's head, indicator 204*c* (e.g., an LED) positioned on a bottom portion of the top surface of the therapy electrode to provide information indicating the electrode should be moved toward the subject's feet, indicator 204*d* (e.g., an LED) positioned on a left-side portion of the top surface of the therapy electrode to provide information indicating the electrode should be moved to the left, and indicator 204*b* (e.g., an LED) positioned on a right-side portion of the top surface of the therapy electrode to provide information indicating the electrode should be moved to the right.

Figure 8C:
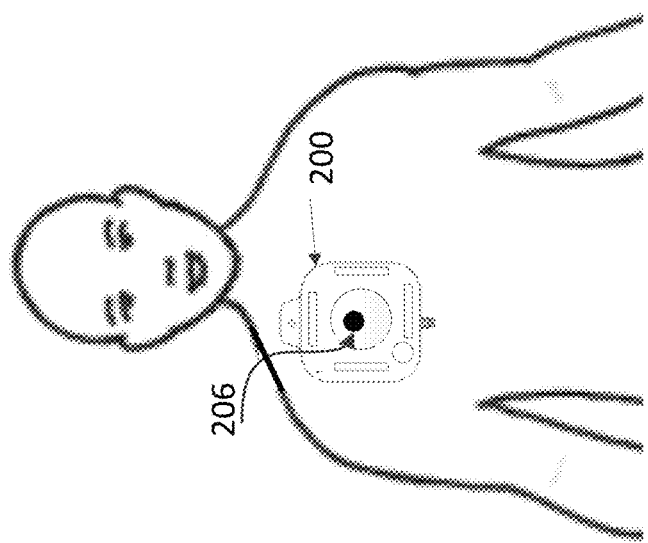
FIGS. 8A-8C are schematic diagrams of the electrode prior to attachment to a subject.
Figure 8B:
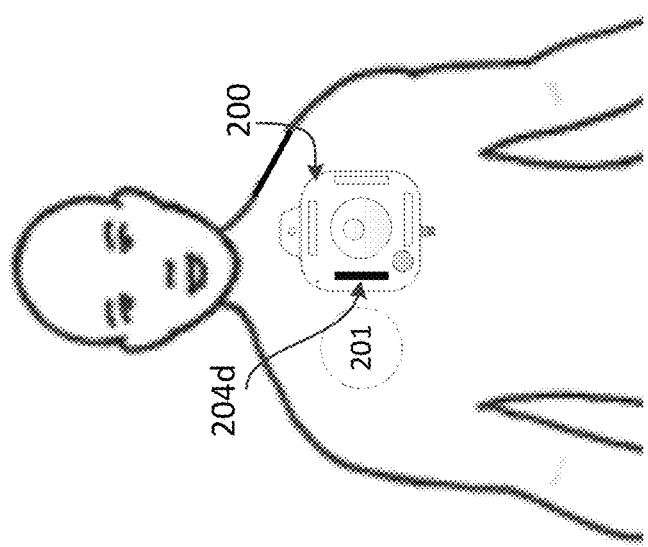
Figure 8A:
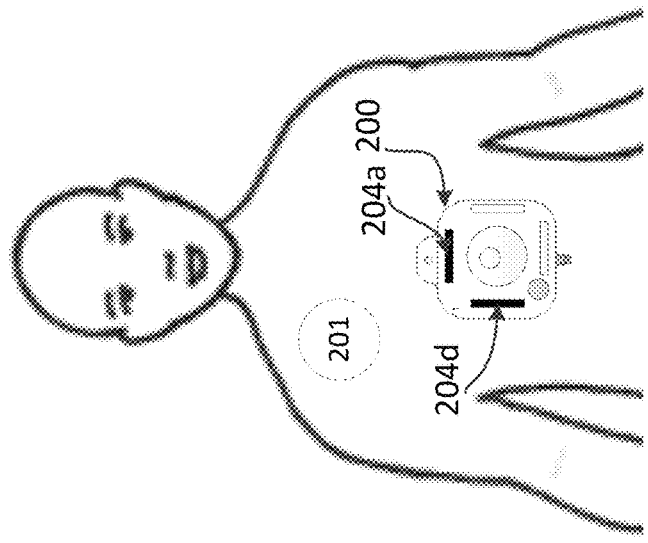

In operation, as shown in FIGS. 8A-8C, the indicators guide the rescuer in placement of the electrode 200 according to an example embodiment of the invention. For example, in FIGS. 8A-8C, the desired location for the electrode is indicated by the dotted circle 201. The camera 202 included in electrode 200 receives an image of the victim and a processor or other computing device determines the location of the electrode relative to the victim's chest based on the image. The processor or other computing device compares the determined location with the desired location (e.g., location 201) and determines whether the electrode is correctly positioned. If the electrode is not correctly positioned, the processor or computing device causes the appropriate indicators on the electrode to be illuminated. For example, as shown in FIG. 8A, the rescuer has the electrode 200 down and to the right of the desired electrode location 201 so the processor or computing device sends a signal to electrode 200 to cause the indicators 204*a* and 204*d* to be illuminated indicating that the electrode 200 should be moved to the left and up from the current location. As shown in FIG. 8B, the rescuer has moved the electrode up, but the electrode is still to the right of the desired location so the processor or computing device causes indicator 204*d* to be illuminated to indicate that the electrode should be moved to the left. Indicator 204*a* is no longer illuminated because the rescuer had moved the electrode up to an appropriate vertical position. As shown in FIG. 8C, the rescuer has moved the electrode to the left and the electrode is appropriately positioned so the processor or computing device causes indicator 206 to be illuminated to indicate that the electrode is correctly positioned and should be affixed to the victim.

Figure 9:
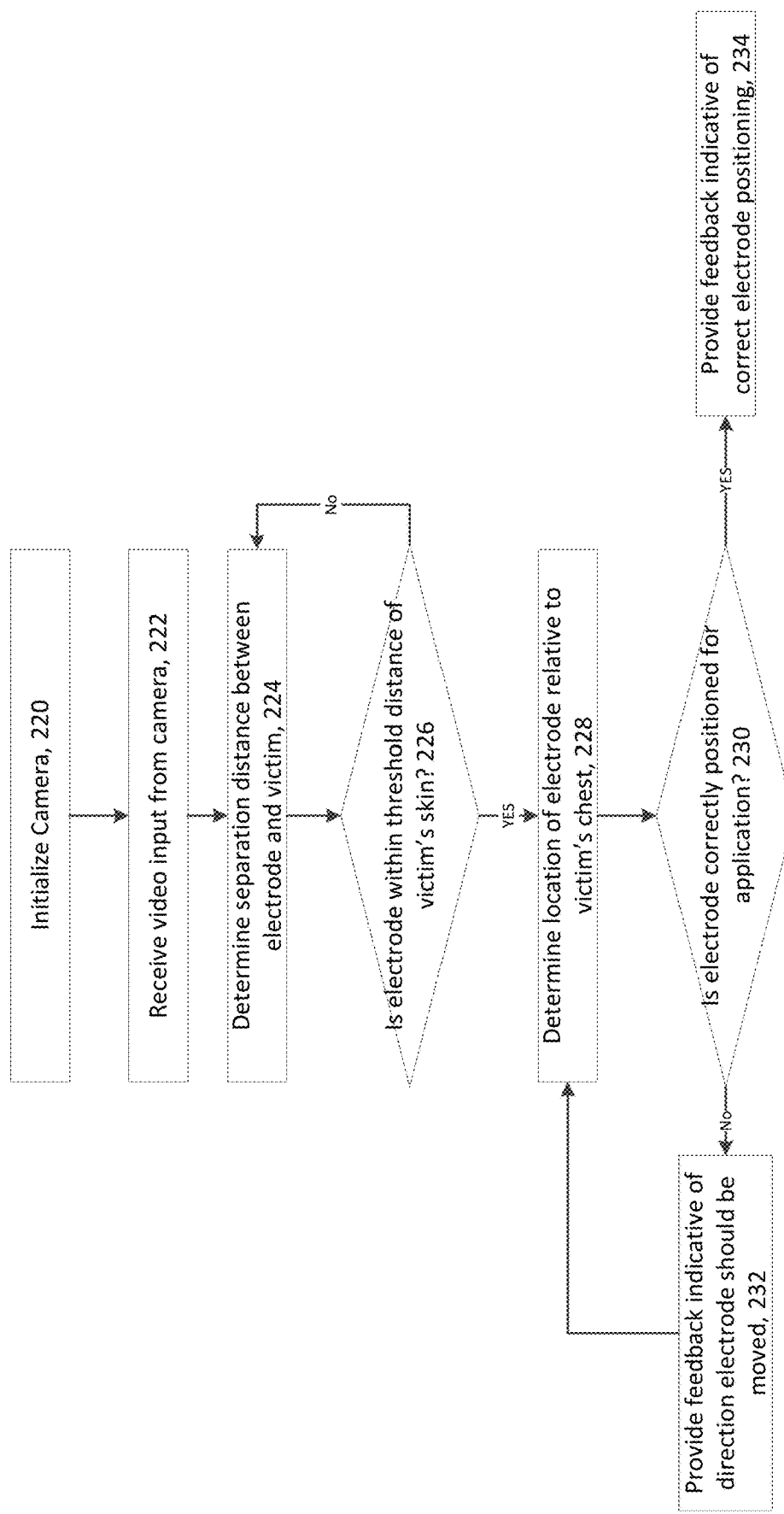
FIG. 9 is a flow chart of a process for providing positioning information to a rescuer prior to the attachment of the electrodes to the subject.

FIG. 9 is a flow chart of a process for providing electrode positioning feedback to a rescuer based on image information received from a camera in the electrode. A processor or computing device initializes the camera (220). For example, the camera can be initialized automatically by the processor or computing device upon removal of the electrodes from the package or upon connection of the electrodes to the defibrillation device. Alternatively, the rescuer can press a button or otherwise provide an input that causes the processor or computing device to initialize the camera. The processor or computing device receives image information from the camera (222). The image information can include still images such as a series of images captured in a time-lapse manner (e.g., by taking an image at a set time interval such as every second, every two seconds, etc.). In some other examples, the image information can include video information. The processor or computing device determines a separation distance between the electrode and the victim (224) and determines if the separation distance is within the threshold distance (226). If the separation distance is greater than a threshold distance the process returns to determining a separation distance between the electrode and the victim based on newly received image information (224). In some examples, feedback can be provided to the rescuer to prompt the rescuer to position the electrode above the victim's chest. If the separation distance is within the threshold distance, the processor or computing device determines a location of the electrode relative to the victim's chest (228) and determines if the electrode is positioned for application (230). For example, a processor may use an image comparison technique to compare the image received in 222 with one or more previously stored images of a subject's chest.

For example, the processor or computing device can use an image comparison technique to align two images with the x and y translation distances providing the direction in which the electrode should be moved. In another example, an image analysis can be used to determine the electrode's location relative to the victim's chest (e.g., by determining location relative to the victim's nipples, shoulders, belly button, etc.). The x and y translation distances can then be determined based on the electrode's current location and the electrode's desired location (e.g., an x-translation and a y-translation from a desired position are determined).

Figure 10:
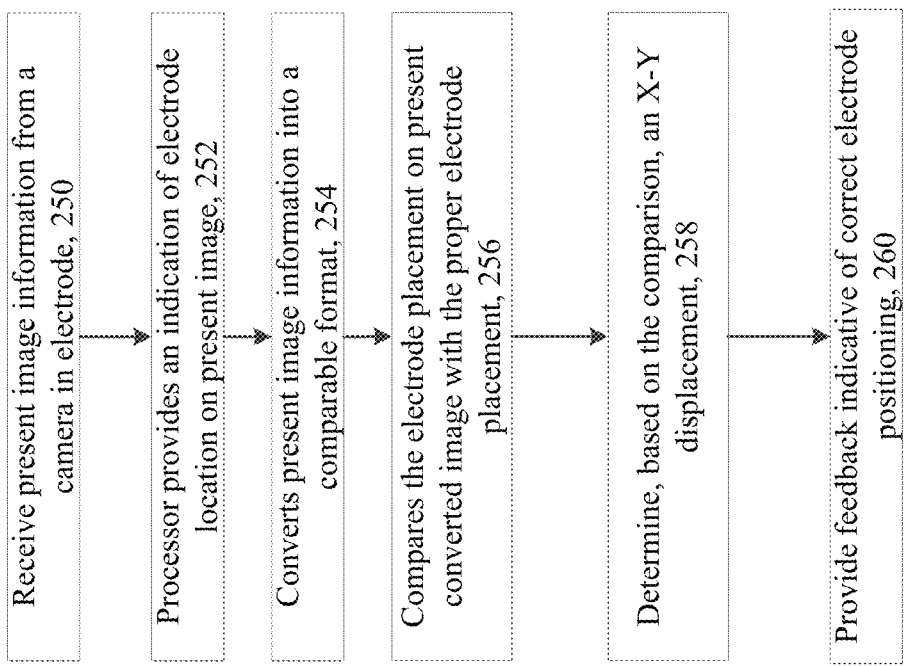
FIG. 10 is a flow chart of a process for providing positioning information.

FIG. 10 is a flow chart of a process for providing electrode positioning feedback to a rescuer based on image information received from a camera in the electrode. A processor receives present image information from a camera in electrode (250). The processor provides an indication of electrode location on present image (252). The processor converts present image information into a comparable format (254). A converter module located in the defibrillator may be configured to provide the conversion. For example, the present image and previously stored images may be converted into one or more formats for the purpose of comparison such as a format based on a key feature extraction algorithm. Key features are certain features of an image such as a subject's nipples, shoulders, belly button, sternum, etc. Key features within an image including their locations within the image may be extracted by using key feature extraction techniques and algorithms known in the art. In an embodiment, the present image and the previously stored images may be scaled prior to key feature extraction. The previously stored images may reside on a local database within the defibrillator or accessible via a communication channel such as a network. The processor compares the electrode placement on present converted image with the proper electrode placement on at least one of previously stored images including surrounding key features (256) and determines, based on the comparison, an X-Y displacement, if any (258). Based on the determination, the processing device can provide feedback indicative or correct electrode positioning (260).

If the electrode is correctly positioned for application (e.g., the electrode is in the correct location), the processor or computing device provides feedback indicating the electrode is in the correct position (234). For example, the processor or computing device can send a signal to an LED to cause the LED to be illuminated indicating correct positioning. In another example, an audio signal can be played to indicate correct positioning. If the electrode is not correctly positioned for application (e.g., the electrode is not in the correct location), the processor or computing device provides feedback indicating the direction in which the electrode should be moved (232). For example, the processor or computing device can send a signal to one or more LEDs on the electrode to cause the LED(s) to be illuminated indicating the direction in which the electrode should be moved. In another example, an audio signal can be played to indicate the direction in which the electrode should be moved.

While in the examples described above, positioning information was provided to the rescuer by a set of LEDs, other devices/methods can be used to provide the information. For example, a display on the defibrillator or on another device could provide an image with an indication of a current location of the electrode and a desired location such that the rescuer could view the display and move the electrode to make the current location align with the desired location. In another example, a monitor or screen on the defibrillator or the electrode can display an image such as an arrow showing a direction in which the rescuer should move the electrode. In another example, audio feedback could be provided by a speaker on the defibrillator or on another device. For example, the audio feedback could include guidance such as "move the electrode towards the victim's head" or "move the electrode to the left." In another example, the electrode could include a different configuration of LEDs to provide guidance to the user. For example, the electrode could include additional LEDs to provide an indication of whether the electrode should be moved by a small amount or by a larger distance.

In some implementations, an electrode can include both a camera and feedback devices to help a user to correctly position the electrodes (e.g., as described herein) and multiple electrically conductive components for measuring impedances to provide the rescuer with information about whether the electrodes are adequately affixed to form the current path between the defibrillator and the victim (e.g., as described herein).

In some aspects, an electrode includes a camera configured to generate image information related to the position of the electrode relative to an subject's chest.

Embodiments can include one or more of the following.

The electrode can also include one or more indicators configured to provide information indicative of whether the electrode is adequately positioned for affixing to the subject's chest based on the image information related to the position of the electrode.

The one or more indicators can include one or more light emitting diodes configured to provide information indicative of correct positioning of the electrode.

The one or more indicators can include a display configured to provide information indicative of correct positioning of the electrode.

The electrode can also include speaker configured to provide information indicative of correct positioning of the electrode.

The one or more indicators can include a first light emitting diode configured to provide information indicating the electrode should be moved toward the subject's head, a second light emitting diode configured to provide information indicating the electrode should be moved toward the subject's feet; a third light emitting diode configured to provide information indicating the electrode should be moved to the left; and a fourth light emitting diode configured to provide information indicating the electrode should be moved to the right.

The camera can be configured to generate video image information.

The camera can be configured to generate image information.

The electrode can include a first electrically conductive element of the electrode configured to accept an electrical defibrillation pulse from the defibrillation device and spread the electrical pulse across the electrically conductive element, from which it is delivered to the subject's chest; a second electrically conductive element of the electrode that is separate from the first electrically conductive element and configured to provide an electrical contact to the subject's chest; a first electrical lead of the electrode connected to the first electrically conductive element of the electrode; and a second electrical lead of the electrode connected to the second electrically conductive element of the electrode, the first and second electrical leads of the electrode providing an output from which information indicative of whether the electrode is affixed to the subject's chest can be obtained.

The information indicative of whether the first electrode is affixed to the subject's chest can include impedance information.

The information indicative of whether the first electrode is affixed to the subject's chest can include resistance information.

The electrode can also include plurality of ECG electrodes.

The electrode can also include a non-conductive backing layer.

The electrode can also include a conductive layer configured to be in electrical contact with the chest of the subject and in electrical contact with an exposed surface of the first electrically conductive element on the other of its surfaces.

The electrode can also include a sensor for use with the defibrillation device that provides an output from which information about the depth of CPR chest compressions can be obtained.

The electrode can also include a sensor for use with the defibrillation device that provides an output from which information about the depth of compressions to the chest during CPR chest compressions can be obtained.

The electrode can also include a sensor for use with the defibrillation device that provides an output from which information about the rate of CPR chest compressions can be obtained.

In some aspects, a method can include receiving image information from a camera in an electrode; determining information about a position of the electrode based on the image information; and providing an indication relating to positioning of the electrode.

Embodiments can include one or more of the following.

Determining information about the positioning of the electrode can include determining an x-translation and a y-translation from a desired position.

Determining information about the position of the electrode can include determining whether the electrode is adequately positioned for application to the victim's chest.

The image information can be a still image.

The image information can be a video.

Providing feedback to the rescuer about the position of the electrode can include sending a signal to cause one or more light emitting diodes on the electrode to be illuminated.

Providing feedback to the rescuer about the position of the electrode can include sending a signal to cause a display device to display information associated with the position.

Providing feedback to the rescuer about the position of the electrode can include generating an audio output.

The method can also include determining an impedance between a first electrically conductive element and a second electrically conductive element of a first electrode and comparing, by a computing device, the impedance to a threshold to determine whether the first electrode is affixed to a subject's chest.

The method can also include providing instructions to a rescuer about application of the electrode upon a determination that the first electrode is not affixed to the subject's chest.

Determining the impedance can include applying a voltage between the first electrically conductive element and the second electrically conductive element of the electrode and measuring a current between the first electrically conductive element and the second electrically conductive element of the electrode resulting from the applied voltage.

In some aspects, a device can include an electronic interface arranged to receive image information from a camera in an electrode, the image information providing information from which information about the position of the electrode relative to an subject's chest can be obtained and provide feedback to a rescuer about the positioning of the electrode based on the received image information.

The device can be further configured to determine a position of the electrode based on the received image information.

The electronic interface can be configured to provide feedback to the rescuer by sending a signal to an indicator in the electrode to cause the indicator to be illuminated when the electrode is adequately positioned for application to the victim's chest.

The electronic interface can be configured to provide feedback to the rescuer by sending signals to one or more indicators in the electrode to cause the indicators to be illuminated to indicate a direction in which the electrode should be moved.

The electronic interface can be configured to provide feedback to the rescuer by sending signals to a display device to cause the display device to indicate a direction in which the electrode should be moved.

The one or more indicators can include a first light emitting diode configured to provide information indicating the electrode should be moved toward the subject's head, a second light emitting diode configured to provide information indicating the electrode should be moved toward the subject's feet, a third light emitting diode configured to provide information indicating the electrode should be moved to the left; and a fourth light emitting diode configured to provide information indicating the electrode should be moved to the right.

The camera can be a video camera in the electrode.

The camera can be a still image camera in the electrode.

The device can also include a processor configured to determine information about the positioning of the electrode by determining an x-translation and a y-translation from a desired position.

The device can also include a processor configured to determine whether the electrode is adequately positioned for application to the victim's chest.

The image information can be a still image.

The image information can be a video input.

The device can also include a speaker configured to provide the feedback to the rescuer about the positioning of the electrode.

The device can also include a processor configured to determine an impedance between a first electrically conductive element and a second electrically conductive element of the electrode and compare the impedance to a threshold to determine whether the first electrode is affixed to an subject's chest.

In some aspects, a device includes a first therapy electrode for use with a defibrillation device. The first therapy electrode includes a first metallic element of the first therapy electrode configured to accept an electrical defibrillation pulse from the defibrillation device and spread the electrical pulse across the metallic element, from which it is delivered to the patient's chest and a second metallic element of the first therapy electrode that is separate from the first metallic element and configured to provide an electrical contact to the patient's chest. The first therapy electrode also includes a first electrical lead of the first therapy electrode connected to the first metallic element of the first therapy electrode and a second electrical lead of the first therapy electrode connected to the second metallic element of the first therapy electrode, the first and second electrical leads of the first therapy electrode providing an output from which information indicative of whether the first therapy electrode is affixed to the patient's chest can be obtained.

Embodiments can include one or more of the following.

The information indicative of whether the first therapy electrode is affixed to the patient's chest can include an impedance measurement.

The information indicative of whether the first therapy electrode is affixed to the patient's chest can include a resistance measurement.

The device can further include a second therapy electrode that includes a first metallic element of the second therapy electrode configured to accept an electrical defibrillation pulse and spread the electrical pulse across the metallic element, from which it is delivered to the patient's chest and a second metallic element of the second therapy electrode that is separate from the first metallic element and configured to provide an electrical contact to the patient's chest. The second therapy electrode also includes a first electrical lead of the second therapy electrode connected to the first metallic element of the second therapy electrode and a second electrical lead of the second therapy electrode connected to the second metallic element of the second therapy electrode, the first and second electrical leads of the first therapy electrode providing an output from which information indicative of whether the first therapy electrode is affixed to the patient's chest can be obtained.

The first therapy electrode can also include a plurality of ECG electrodes.

The first therapy electrode can also include a non-conductive backing layer.

The first therapy electrode can also include a conductive layer configured to be in electrical contact with the chest of the patient and in electrical contact with an exposed surface of the first metallic element on the other of its surfaces.

The conductive layer can include a conductive layer selected from the group consisting of a conductive viscous liquid, an electrolyte, a solid conductive gel, and hydrogel.

The metallic element can be made from stainless steel.

The first and second metallic elements can be encapsulated by the flexible nonconductive element.

The electrode can also include a first peripheral adhesive region outside of the area of the first and second metallic contacts configured to adhere to the chest of the patient.

The device can also include a sensor for use with the defibrillation device that provides an output from which information about the depth of CPR chest compressions can be obtained.

The sensor can be an accelerometer.

The device further can also include a sensor for use with the defibrillation device that provides an output from which information about the depth of compressions to the chest during CPR chest compressions can be obtained.

The device further can also include a sensor for use with the defibrillation device that provides an output from which information about the rate of CPR chest compressions can be obtained.

In some additional aspects, a method includes determining an impedance between a first metallic element and a second metallic element of a first therapy electrode and comparing, by a computing device, the impedance to a threshold to determine whether the first therapy electrode is affixed to a patient's chest.

Embodiments can include one or more of the following.

The method can also include determining an impedance between a first metallic element and a second metallic element of a second therapy electrode and comparing, by the computing device, the determined impedance to the threshold to determine whether the second therapy electrode is affixed to the patient's chest.

The method can also include determining an impedance between the first metallic element of the first therapy electrode and the first metallic element of the second therapy electrode and comparing, by the computing device, the determined impedance to second threshold to determine whether the first and second therapy electrodes are adequately affixed to the patient's chest.

The first threshold can be between about 1 and 10 kOhms and the second threshold can be between about 250 and 300 Ohms.

The method can also include providing instructions to a rescuer about application of the therapy electrode upon a determination that the first therapy electrode is not affixed to the patient's chest.

The first threshold can be about 10 kOhms.

Determining the impedance can include applying a voltage between the first a first metallic element and a second metallic element of a first therapy electrode and measuring a current between the first metallic element and a second metallic element of the first therapy electrode resulting from the applied voltage.

Many other implementations of the invention other than those described above are within the invention, which is defined by the following claims.

What is claimed is:

1. A computer implemented method for guiding a rescuer in placement of a defibrillation electrode on a chest of a patient, the method comprising:
    initializing one or more cameras disposed on the defibrillation electrode;

capturing image information via the one or more cameras disposed on the defibrillation electrode, wherein each image in a series of images is acquired by the one or more cameras after a set time interval;

determining a separation distance between the defibrillation electrode and the chest of the patient and comparing the separation distance to a threshold distance;

determining whether the separation distance is below the threshold distance and, once the separation distance is below the threshold distance, determining a current location of the defibrillation electrode based on the series of images;

providing positioning feedback via at least one output device, wherein the positioning feedback includes instructions to move the defibrillation electrode toward a preferred location for placement on the patient.

2. The method of claim 1, wherein determining the current location of the defibrillation electrode comprises determining an x-translation distance and a y-translation distance between the current location of the defibrillation electrode and the preferred location for the placement of the defibrillation electrode.

3. The method of claim 1, wherein determining the current location comprises comparing the generated series of images to previously stored images.

4. The method of claim 3, wherein comparing the generated series of images to previously stored images comprises comparing one or more identified features in the series of images to the previously stored images, which include the defibrillation electrode positioned in the preferred location for the placement on the chest of the patient and adjacent to one or more features of the patient.

5. The method of claim 4, wherein the one or more features of the patient include at least one of: nipples, shoulders, a belly button, and a sternum of the patient.

6. The method of claim 1, wherein providing positioning feedback includes displaying the current location of the defibrillation electrode relative to the chest of the patient via the at least one output device.

7. The method of claim 6, wherein providing positioning feedback includes determining whether the current location of the defibrillation electrode corresponds to the preferred location for the placement of the defibrillation electrode.

8. The method of claim 7, further comprising providing an indication when the current location of the defibrillation electrode corresponds to the preferred location for the placement of the defibrillation electrode.

9. The method of claim 8, further comprising determining a current location of a second defibrillation electrode based on one or more features of the patient in the series of images.

10. The method of claim 9, further comprising providing positioning feedback to the at least one output device, wherein the positioning feedback includes instructions to move the second defibrillation electrode to a preferred location for the placement on the chest of the patient.

11. The method of claim 10, further comprising providing an indication when the current location of the second defibrillation electrode corresponds to the preferred location for the placement of the second defibrillation electrode.

12. The method of claim 11, further comprising providing one or more defibrillation shock to the patient in response to a determination that the defibrillation electrode and the second defibrillation electrode are in their respective preferred locations on the chest of the patient.

13. The method of claim 1, wherein providing positioning feedback includes indicating a direction via the at least one output device, relative to the current location of the defibrillation electrode, in which the rescuer should move the defibrillation electrode.

14. The method of claim 13, wherein the at least one output device is a display and the positioning feedback comprises visual feedback.

15. The method of claim 14, wherein the visual feedback comprises illuminating one or more indicators disposed on the defibrillation electrode such that one or more of the one or more indicators illuminate to indicate a direction in which the rescuer should move the defibrillation electrode.

16. The method of claim 15, wherein the one or more indicators comprise:
a first light emitting diode configured to provide an indication that the rescuer should move the defibrillation electrode toward a head of the patient;
a second light emitting diode configured to provide an indication that the rescuer should move the defibrillation electrode toward feet of the patient;
a third light emitting diode configured to provide an indication that the rescuer should move the defibrillation electrode to the left of the current location; and
a fourth light emitting diode configured to provide an indication that the rescuer should move the defibrillation electrode to the right of the current location.

17. The method of claim 1, wherein providing positioning feedback includes playing audible feedback via a speaker of the at least one output device.

18. The method of claim 1, wherein the one or more cameras are video cameras.

19. The method of claim 18, wherein the series of images captured by the or more video cameras are video data.

20. The method of claim 1, wherein the one or more cameras are still image digital cameras.

21. The method of claim 20, wherein the series of images captured by the or more video cameras are still images.

22. The method of claim 21, wherein the still images comprise images captured in a time-lapse manner.

* * * * *

UNITED STATES PATENT AND TRADEMARK OFFICE
CERTIFICATE OF CORRECTION

| | |
|---|---|
| PATENT NO. | : 11,224,738 B2 |
| APPLICATION NO. | : 16/441673 |
| DATED | : January 18, 2022 |
| INVENTOR(S) | : Ziad F. Elghazzawi and Gary A. Freeman |

It is certified that error appears in the above-identified patent and that said Letters Patent is hereby corrected as shown below:

In the Claims

Claim 19, Column 16, Line 45 - after "the" insert -- one --
Claim 21, Column 16, Line 49 - after "the" insert -- one --

Signed and Sealed this
Fourteenth Day of June, 2022

Katherine Kelly Vidal
*Director of the United States Patent and Trademark Office*